United States Patent [19]

Saitoh et al.

[11] Patent Number: 5,500,437
[45] Date of Patent: Mar. 19, 1996

[54] MICROBICIDES

[75] Inventors: Yasuhiko Saitoh, Atsugi; Yasuo Iwata; Seiichi Kuzuma, both of Sagamihara; Yoshihide Nakajima, Akashi; Kanji Yokomizo, Nishinomiya, all of Japan

[73] Assignees: Ciba-Geigy, AG, Basle, Switzerland; Ube Industries Limited, Yamaguchi; Hokko Chemical Industry Co., Ltd., Tokyo, both of Japan

[21] Appl. No.: 427,722

[22] Filed: Apr. 24, 1995

Related U.S. Application Data

[63] Continuation of Ser. No. 205,747, Mar. 4, 1994, abandoned.

[30] Foreign Application Priority Data

Mar. 4, 1993 [JP] Japan ................................. 5-069283

[51] Int. Cl.$^6$ ............................. A01N 43/36; A01N 43/50
[52] U.S. Cl. ................................. 514/397; 514/422
[58] Field of Search ........................ 514/397, 422

[56] References Cited

U.S. PATENT DOCUMENTS 4,705,800 11/1987 Nyfeler et al. .......................... 514/422
5,198,456 3/1993 Dutzmann et al. ..................... 514/383

OTHER PUBLICATIONS

Anonymous, Chem. Abstr., vol. 112, No. 7, 12 Feb. 1990, Abstract No. 50497u, "Fungicide Combination Preparations", p. 260, Res.. Discl. vol. 307, 1989, No. 781.

Hirata et al., Chem. Abstr., vol. 104, No. 21, 26 May 1986, Abstract No. 186418m Abstracting JP-A-60 260 572.

The Pesticide Manual, p. 653, Ninth Edition, Editor Charles R. Worthing, et al. Published by The British Crop Protection Council (1987).

*Primary Examiner*—Allen J. Robinson
*Attorney, Agent, or Firm*—Wenderoth, Lind & Ponack

[57] ABSTRACT

A disinfectant composition comprising as active ingredients 4-(2,2-difluoro-1,3-benzo-dioxol-4-yl)pyrrole-3-carbonitrile and penta-4-enyl-N-furfuryl-N-imidazol-1-ylcarbonyl-DL-homoalaninate exhibits high synergistic effect by the joint use of the two active ingredients and has remarkably high effect in a low amount against Bakanae disease, blast, leaf spot, loose smut, Septoria leaf blight, snow mold on cereals such as rice, wheat, barley etc.

7 Claims, No Drawings

MICROBICIDES

This application is a continuation of now abandoned application Ser. No. 08/205,747, filed Mar. 4, 1994.

The present invention relates to a microbicidal composition comprising as active ingredients 4-(2,2-difluoro-1,3-benzodioxol-4-yl)pyrrole-3-carbonitrile (hereinafter called compound A) and penta-4-enyl-N-furfuryl-N-imidazol-1-ylcarbonyl-DL-homoalaninate (hereinafter called compound B).

By disinfecting seeds of various cereal plants such as rice, wheat, barley etc. prior to seeding thereof with said composition, it is possible to kill phytopathogenic fungi, which are parasitic on the seeds, and to protect seeds from the soil-epidemic germs which live in soil and invade seeds and young seedlings after the seeding to cause damage. Therefore, the disinfectant composition is useful in agricultural and horticultural fields.

It is known by Japanese Patent Kokai Sho 62-483 and Brighton Crop Protection Conference "Pests and Diseases 1990", Vol. 2, pp. 399–406 that compound A has a broad activity spectrum against phytopathogenic fungi such as Botrytis, Monilinia, Sclerotinia, Rhizoctonia, Alternaria etc and shows high controlling effect in the form of a spray for leaves and stems. It is also known by "Entrusted trial test data book for rice fungicides" by Japan Plant Protection Association, 1992, Vol. 34, pp. 362–458 and Brighton Crop Protection Conference "Pests and Diseases 1990", Vol. 2 (1990), pp. 825–830 that the compound shows high seed disinfection effect against rice diseases such as Bakanae disease, blast, leaf spot and also diseases such as loose smut, Septoria leaf blight, snow mold etc.

On the other hand, compound B, the other active ingredient of the present invention, is known by "Agricultural Chemicals Handbook, 1992" published by Japan Plant Protection Association as of Jul. 30, 1992, pp. 224–549 to be useful as for a seed disinfectant against rice Bakanae disease, rice blast, rice leaf spot and various diseases on wheat and vegetables.

However, the mixture of compound A and compound B has not been predescribed. Until now, mixtures of a benzimidazole derivative and thiuram have been widely used as seed disinfectants. These compounds are known by "Agricultural Chemicals Handbook, 1992" published by Japan Plant Protection Association on Jul. 30, 1992), pp. 192–198 and 171–173. However, as the result of long and continuous use of said mixtures in recent years, a problematic Bakanae disease germ has appeared which is resistant to benzimidazole type microbicides.

Furthermore, the benzimidazole compound has poor permeability and thus shows somewhat lesser effect on the seeds infected in depth.

Since the conventional seed disinfectants are not always satisfactory in their effects, more improved agents are highly desired.

The present invention is to offset the above mentioned faults and to provide a novel and stable composition, e.g. for seed disinfectant, which is effective to the fungi resistant to said benzimidazole derivatives even with a low amount.

The combination of compound A and compound B expressed by the following formulae meets the purpose to attain the high seed disinfection effect. Namely, the gist of the present invention resides in a seed disinfectant comprising as active ingredients 4-(2,2-difluoro-1,3-benzodioxol-4-yl)pyrrole-3-carbo-nitrile and penta-4-enyl-N-furfuryl-N-imidazol-1-ylcarbonyl-DL-homoalaninate.

Compound A:

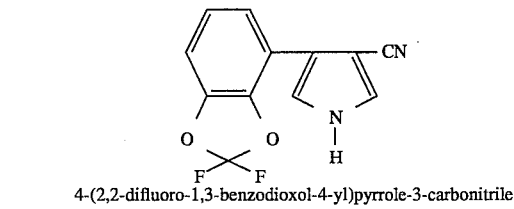

4-(2,2-difluoro-1,3-benzodioxol-4-yl)pyrrole-3-carbonitrile

Compound B:

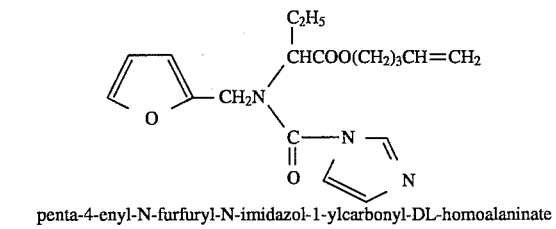

penta-4-enyl-N-furfuryl-N-imidazol-1-ylcarbonyl-DL-homoalaninate

FORMULATION METHOD

To prepare the composition of the present invention, there are combined both or each of the active ingredients of the present invention with a suitable carrier, i.e. extender and/or auxiliaries, e.g. suffactants, binding agents, stabilizers etc. which will be formulated into a wettable powder, emulsion, flowable agent, wettable granule etc. to obtain a one-agent type seed disinfectant or two-agent type seed disinfectant composition.

The mixing ratio by weight of the active ingredients of the present invention is 0.1–20 parts of compound B to 1 part of compound A. It may be varied depending on the application condition. Preferred ratios are A:B=10:1 to 1:10, especially preferred A:B=2:1 to 1:10. Typical ready-for-use mixtures comprise ratios of A:B=1:10, 1:4, 1:3, 2:3 and 1:1. Carriers to be used can be any solid or liquid substances commonly used for the preparation of agricultural formulations. For instance, as solid carriers there may be exemplified mineral powders (Kaolin, bentonitc, clay, talc, diatomaceous earth, silica, vermiculite, calcium carbonate etc), natural polymers (wheat powder, starch, crystal cellulose, carboxymethyl cellulose, gelatin etc), sugars (glucose, maltose, lactose, sucrose etc), ammonium sulfate, urea etc.

Liquid carriers may be exemplified by water, ethylalcohol, ethyleneglycol, propyleneglycol, benzylalcohol, benzene, toluene, xylene, methylnaphthalene, acetone, methylethylketone, cyclohexane, ethyl acetate, butyl acetate, ethyleneglycol acetate, propyleneglycol monomethylether, dipropyleneglycol monomethylether, hexane, petroleum ether, solvent naphtha, Kerosene, light oil etc.

In the formulation of a wettable powder, flowable agent, emulsion etc, surfactants or emulsifiers are used for emulsification, distribution, solubilization, wetting, foaming and dispersing. Examples of such surfactants are non-ionic, anionic, cationic and amphoteric types.

Furthermore, various additives may be added, such as antioxidants, light-decomposition preventing agents, physical property improvers, stabilizers of the active ingredients, viscosity controllers, anti-freezing agents etc.

Furthermore, other fungicidal ingredients, insecticidal ingredients and plant growth regulating ingredients may be mixed with the seed disinfectant of the present invention.

FORMULATION EXAMPLES

The term part used in the examples means part by weight.

Example 1 (Flowable Agent)

| | |
|---|---|
| compound A | 1 part |
| compound B | 10 parts |
| polyoxyethylenenonylphenylether | 1 part |
| sodium lignin sulfonate | 4 parts |
| water | 74 parts |

The above ingredients are homogeneously mixed and dispersed by a homomixer, to which 10 parts of 2% xanthane gum aqueous solution are added to obtain a flowable agent.

Example 2 (Flowable Agent)

| | |
|---|---|
| compound A | 5 parts |
| compound B | 5 parts |
| polyoxyethylenenonylphenylether | 1 part |
| sodium lignin sulfonate | 4 parts |
| water | 75 parts |

The above ingredients are homogeneously mixed and dispersed by a homomixer, to which 10 parts of 2% xanthane gum aqueous solution are added to obtain a flowable agent.

Example 3 (Wettable Powder)

| | |
|---|---|
| compound A | 1 part |
| compound B | 10 parts |
| white carbon | 20 parts |
| sodium lauryl sulfate | 3 parts |
| calcium lignin sulfonate | 2 parts |
| clay | 64 parts |

The above ingredients are mixed and sufficiently pulverized to obtain a wettable powder.

Example 4 (Flowable Agent)

agent (1)

| | |
|---|---|
| compound A | 5 parts |
| polyoxyethylenenonylphenylether | 1 part |
| sodium lignin sulfonate | 4 parts |
| water | 80 parts |

The above ingredients are homogeneously mixed and dispersed by a homomixer, to which 10 parts of 2% xanthane gum aqueous solution are added to obtain a flowable agent.

agent (2)

| | |
|---|---|
| compound B | 20 parts |
| polyoxyethylenenonylphenylether | 1 part |
| sodium lignin sulfonate | 4 parts |
| water | 65 parts |

The above ingredients are homogeneously mixed and dispersed by a homomixer, to which 10 parts of 2% xanthane gum aqueous solution are added to obtain a flowable agent.

As mentioned above, a two-agent type formulation is thus prepared.

BIOLOGICAL EXAMPLES

Example (Method of Use)

Among the methods of disinfection by using the above mentioned or similar formulation examples, the preferred methods are a method of dipping unhulled seed (e.g. rice seed) into a disinfectant composition according to the present invention diluted with water by 10–1000 fold, wherein the volume of the diluted disinfectant is 0.7–4 times the volume of the seeds; a method of coating the unhulled seeds with 0.1–4.0% by weight (based on the dry seed weight) of wettable powder itself; a method of spraying the disinfectant diluted by 5–40 folds to the seeds with a spray designed specifically for said purpose, wherein the amount to be sprayed is 3% by weight of the seeds. In the dipping method mentioned above, the unhulled seeds can be dipped in the disinfectant of a lower concentration (diluted by 100–1000 folds) for a longer time (6–72 hours) or of a higher concentration (diluted by 10–100 folds) for a shorter period 10–30 minutes).

By using a two-agent type formulation or two commercially available formulations each comprising either one of the active ingredients of the present invention, a subsequent dipping method comprising dipping seeds in a formulation containing one of the two active ingredients followed by dipping to another formulation containing the other active ingredient provides similar disinfection effect. Also, simultaneous treatment using a mixture of both formulations in a desired mixing ratio is possible, in which seeds are dipped into, coated or sprayed with the mixed formulations.

The disinfectant composition of the present invention, firstly showing high synergistic effect by the joint use of the two active ingredients, has remarkably high effect against rice diseases such as Bakanae disease, blast, leaf spot and wheat diseases such as loose smut, Septoria leaf blight, snow mold etc. In particular, the disinfectant shows perfect controlling effect, which has been long waited for, against rice Bakanae disease and leaf spot even with a lower amount of the agent. Secondly, the present disinfectant shows high effect against benzimidazole resistant strain of Bakanae disease fungus as high as the effect against benzimidazol sensitive strain of Bakanae disease fungus.

BIOLOGICAL EXAMPLES

The seed disinfection effect of the composition of the present invention is exemplified by the following tests.

Test 1

Naturally infected unhulled rice seeds (cultivar: Nipponbare), collected from the paddy field infected heavily by rice Bakanae pathogenic germ (benzimidazole resistant-strain) were dipped for 24 hours at 15° C. into the flowable agent prepared in accordance with example 1 and diluted to a predetermined concentration to disinfect the seeds, wherein the ratio of unhulled seeds to solution (V/V) was 1:1.

After the treatment, the test solution was removed and the seeds were dipped in tap water in an amount twice as much as the unhulled seeds for 5 days at 15° C. Thereafter, the treated unhulled rice seeds were treated to hasten germination at 30° C. for 15 hours and seeded into commercially available artificial granular soil in an amount of 2.5 gs of the seeds per one block (120 cm$^2$). After emergence at 32° C. for 2 days, the test seeds were kept in a green-house.

On the 30th day after the seeding, the number of infected seedlings and that of non-infected seedlings were counted. The incidence of infection (%) of the seedlings and percent control were calculated by the following equations.

$$\text{incidence of infection (\%)} = \frac{\text{Number of the infected plants}}{\text{total number of plants}} \times 100$$

-continued $$\text{percent control} = \frac{\text{incidence of infection in untreated minus incidence of infection in treated}}{\text{incidence of infection in untreated}} \times 100$$

Side effects were also investigated based on the germination ratio, growth behavior etc (same applies to the below mentioned tests). Results are shown in Table 1.

TABLE 1

| Treated block | Active ingredients | Concentration (ppm) | percent control | Side Effects |
|---|---|---|---|---|
| Invention block | Compounds A & B | 25 + 250 | 100 | none |
|  |  | 12.5 + 125 | 100 | none |
| Comparison block | Compound A | 25 | 90 | none |
|  |  | 12.5 | 80 | none |
|  | Compound B | 250 | 92 | none |
|  |  | 125 | 83 | none |
| Non-treated block | — | — | 0 (58.8) | — | note:
The number in parentheses shows the incidence of infection (%) in the non-treated block.

Test 2

Naturally infected unhulled rice seeds (cultivar: Sasanishiki) collected from a paddy field infected heavily by rice leaf spot pathogenic germ were dipped for 24 hours at 15° C. into the flowable agent prepared in accordance with example 1 and diluted to a predetermined concentration to disinfect the seeds, wherein the ratio of unhulled seeds to solution (V/V) was 1:1.

After the treatment, the test disinfectant solution was removed and the seeds were dipped in tap water in an amount twice as much as the unhulled seed for 5 days at 15° C. Thereafter, the treated unhulled rice seeds were treated to hasten germination at 30° C. for 15 hours and seeded into commercially available artificial granular soil in an amount of 2.5 gs of the seeds per one block (120 cm$^2$). After emergence treatment at 32° C. for 2 days, the test seeds were kept in a green-house.

On the 25th day after the seeding, the number of infected seedlings and that of non-infected seedlings were counted. The incidence of infection (%) of the seedlings and the percent control were calculated by the equations according to Test 1.

Results are shown in Table 2.

TABLE 2

| Treated block | Active ingredients | Concentration (ppm) | percent control | Side Effects |
|---|---|---|---|---|
| Invention block | Compounds A & B | 25 + 250 | 100 | none |
|  |  | 12.5 + 125 | 100 | none |
| Comparison block | Compound A | 25 | 89 | none |
|  |  | 12.5 | 88 | none |
|  | Compound B | 250 | 82 | none |
|  |  | 125 | 73 | none |
| Non-treated block | — | — | 0 (11.5) | — | note:
The number in parentheses shows the incidence of infection (%) in the non-treated block.

Test 3

Naturally infected unhulled rice seeds (cultivar: Nipponbare), collected from a paddy field infected heavily by rice Bakanae pathogenic germ were dipped for 24 hours at 20° C. into the flowable agent prepared in accordance with example 1 and diluted to a predetermined concentration to disinfect the seeds, wherein the ratio of unhulled seeds to solution (V/V) was 1:1.

After the treatment, the test disinfectant solution was removed and the seeds were dipped in tap water in an amount twice as much as the unhulled seed for 4 days at 20° C. Thereafter, the treated unhulled rice seeds were treated to hasten germination at 30° C. for 15 hours and seeded into commercially available artificial granular soil in an mount of 3 gs of the seeds per one block (30 cm$^2$). After emergence treatment at 32° C. for 2 days, the test seeds were kept in a green-house.

On the 30th day after the seeding, the number of infected seedlings and that of non-infected seedlings were counted. The incidence of infection (%) of the seedlings was calculated according to Test 1. The test was repeated three times and their average was taken as the incidence of infection given below.

Results are shown in Table 3.

TABLE 3

| Treated block | Active ingredients | Concentration (ppm) | Incidence of infection (%) | Side Effects |
|---|---|---|---|---|
| Invention block | Compounds A & B | 50 + 500 | 0.0 | none |
|  |  | 25 + 250 | 0.0 | none |
|  |  | 13 + 125 | 0.3 | none |
|  |  | 6 + 63 | 0.5 | none |
| Comparison block | Compound A | 50 | 2.4 | none |
|  |  | 25 | 5.7 | none |
|  |  | 13 | 8.8 | none |
|  |  | 6 | 11.6 | none |
|  | Compound B | 500 | 1.3 | none |
|  |  | 250 | 1.9 | none |
|  |  | 125 | 3.4 | none |
|  |  | 63 | 6.5 | none |
| Non-treated block | — | — | 51.7 | — |

Test 4

Naturally infected unhulled rice seeds (cultivar: Yamabiko), collected from an paddy field infected heavily by rice leaf spot pathogenic germ were treated with a slurry of the flowable agent prepared according to Example 1 by mixing Compound A and Compound B and diluted with the below mentioned concentrations. The unhulled rice was dried in the air. After the treatment, the test rice was dipped in tap-water in an amount twice as much as the volume of the test seeds for 5 days at 20° C. Thereafter, the treated unhulled rice seeds were treated to hasten germination at 30° C. for 15 hours and seeded into commercially available artificial granular soil in an amount of 3 gs of the seeds per one block (30 cm$^2$). After emergence treatment at 32° C. for 2 days, the test seeds were kept in a green house.

On the 30th day after the seeding, the number of infected seedlings and that of non-infected seedlings were counted. The incidence of infection (%) of the seedlings of each test block was calculated in the same manner as Test 3. The test was repeated three times and their average was taken as the incidence of infection given below.

Results are shown in Table 4.

TABLE 4

| Active Ingredients | | Concentration (ppm) | Incidence of infection (%) | Side Effects |
|---|---|---|---|---|
| Invention block | Compounds A & B | 5 + 50 | 0.7 | none |
| | | 2.5 + 25 | 0.9 | none |
| | | 1.3 + 13 | 1.1 | none |
| | | 0.6 + 6 | 0.9 | none |
| Comparison block | Compound A | 5 | 2.0 | none |
| | | 2.5 | 1.3 | none |
| | | 1.3 | 2.2 | none |
| | | 0.6 | 2.6 | none |
| | Compound B | 50 | 4.2 | none |
| | | 25 | 4.9 | none |
| | | 13 | 6.1 | none |
| | | 6 | 9.1 | none |
| Non-treated block | — | — | 45.2 | — |

Test 5

Naturally infected unhulled rice seeds (cultivar: Nipponbare), collected from a paddy field infected heavily by Bakanae pathogenic germ were treated with a slurry of the flowable agent prepared according to Example 1 by mixing Compound A and Compound B and diluted to the predetermined concentrations (3% by weight agent of dry unhulled rice). The unhulled rice was dried in the air. After the treatment, the test rice was dipped in tap-water in an amount twice as much as the volume of the test seeds for 5 days at 20° C. Thereafter, the treated rice seeds were treated to hasten germination at 30° C. for 15 hours and seeded into commercially available artificial granular soil in an amount of 3 gs of the seeds per one block (30 cm$^2$). After emergence treatment at 32° C. for 2 days, the test seeds were kept in a greenhouse.

On the 30th day after the seeding, the number of infected seedlings and that of non-infected seedlings were counted. The incidence of infection (%) of the seedlings of each test block was calculated in the same manner as Test 3. The test was repeated three times and their-average was taken as the incidence of infection given below.

Results are shown in Table 5.

TABLE 5

| Active Ingredient | | Concentration (ppm) | Incidence of infection (%) | Side Effects |
|---|---|---|---|---|
| Invention block | Compounds A & B | 5 + 50 | 2.1 | none |
| | | 2.5 + 25 | 1.8 | none |
| | | 1.3 + 13 | 2.1 | none |
| | | 0.6 + 6 | 1.4 | none |
| Comparison block | Compound A | 5 | 27.4 | none |
| | | 2.5 | 17.9 | none |
| | | 1.3 | 12.2 | none |
| | | 0.6 | 17.6 | none |
| | Compound B | 50 | 5.4 | none |
| | | 25 | 8.8 | none |
| | | 13 | 17.9 | none |
| | | 6 | 20.3 | none |
| Non-treated block | — | — | 50.4 | — |

We claim:

1. A microbicidal composition which comprises A) 4-(2,2-difluoro-1,3-benzodioxol-4-yl)pyrrole-3-carbonitrile and B) penta-4-enyl-N-furfuryl-N-imidazol-l-yl-carbonyl-DL-homoalaninate, said components A) and B) being present in the composition in a weight ratio which exhibits synergistically enhanced activity of 1 part of A) to 0.1–20 parts of B), and a suitable carrier.

2. The composition according to claim 1 wherein the ratio is A:B=10:1 to 1:10.

3. The composition according to claim 2 wherein the ratio is A:B=2:1 to 1:10.

4. A process for controlling and preventing plant diseases occurring in cereals and susceptible to control with a combination of A) and B) as defined below which comprises applying onto cereals, their seeds or the locus of their growth in either sequence of synergistic effective amounts of a combination of A) 4-(2,2-difluoro-1,3-benzodioxol-4-yl)pyrrole-3-carbonitrile and B) penta-4-enyl-N-furfuryl-N-imidazol-1-ylcarbonyl-DL-homoalanate, the weight ratio of A) to B) being 1 part of A) to 0.1–20 parts of B).

5. The process according to claim 4 wherein the cereals are rice, wheat or barley.

6. The process according to claim 4 wherein the seeds are treated prior to seeding.

7. The process according to claim 4 wherein A) and B) are used in combination together with a suitable carrier.

* * * * *